United States Patent [19]

Jones et al.

[11] Patent Number: 4,917,900
[45] Date of Patent: Apr. 17, 1990

[54] CONTROLLED RELEASE FORMULATIONS CONTAINING ZIDOVUDINE

[75] Inventors: Harry P. Jones; Robert J. Mackey; Michael J. D. Gamlen, all of Dartford, England

[73] Assignee: Burroughs Wellcome Co., Research Triangle Park, N.C.

[21] Appl. No.: 173,261

[22] Filed: Mar. 25, 1988

[30] Foreign Application Priority Data

Mar. 27, 1987 [GB] United Kingdom ............... 8707421

[51] Int. Cl.$^4$ ............................................. A61K 9/16
[52] U.S. Cl. .................... 424/493; 424/490; 424/492; 424/494; 424/495; 424/497
[58] Field of Search ............... 424/490, 492, 493, 494, 424/495

[56] References Cited

U.S. PATENT DOCUMENTS 4,724,232  2/1988  Rideout et al. .................. 514/50

FOREIGN PATENT DOCUMENTS

| | | |
|---|---|---|
| 0122815 | 10/1984 | European Pat. Off. . |
| 0053580 | 7/1985 | European Pat. Off. . |
| 0196185 | 10/1986 | European Pat. Off. . |
| 0080341 | 10/1987 | European Pat. Off. . |
| 145365 | 7/1920 | Fed. Rep. of Germany . |
| 8300435 | 2/1983 | PCT Int'l Appl. . |
| 1384887 | 2/1975 | United Kingdom . |
| 1393374 | 5/1975 | United Kingdom . |
| 1444890 | 8/1976 | United Kingdom . |
| 2086725 | 5/1982 | United Kingdom . |
| 2087235 | 5/1982 | United Kingdom . |
| 2107214A | 4/1983 | United Kingdom . |
| 2123695 | 2/1984 | United Kingdom . |
| 2157170 | 10/1985 | United Kingdom . |
| 2178313 | 2/1987 | United Kingdom . |

OTHER PUBLICATIONS

Lehmann, et al., Drugs Made in Germany, reprint from: vol. XVI, pp. 126–136, (1973).
Christina Eskilson, Controlled Release by Microencapsulation, pp. 33–36 & 39, Manu. Chem., Mar. 1985.
Christina Eskilson, Controlled Release by Microencapsulation, pp. 49, 51 & 53, Manu. Chem., Apr. 1985.

*Primary Examiner*—Thurman K. Page
*Attorney, Agent, or Firm*—Donald Brown

[57] ABSTRACT

The invention relates to pharmaceutical formulations comprising discrete units of zidovudine provided with a controlled release coating in which the said units are preferably in the form of spheroids.

10 Claims, No Drawings

CONTROLLED RELEASE FORMULATIONS CONTAINING ZIDOVUDINE

The present invention relates to controlled release pharmaceutical formulations comprising 3'-azido-3'-deoxythymidine, and their use for the treatment or prophylaxis of certain viral infections more particularly human retroviral infections such as Acquired Immune Deficiency Syndrome (AIDS).

AIDS is an immunosuppressive of immunodestructive disease that predisposes subjects to fatal opportunistic infections. Characteristically, AIDS is associated with a progressive depletion of T-cells, especially the helper-inducer subset baring the OKT[4] surface marker.

Human Immunodeficiency Virus (HIV) has been reproducibly isolated from patients with AIDS or with signs and symptoms that frequently precede AIDS. HIV is cytopathic and appears to preferentially infect and destroy OKT[4]-bearing T-cells, and it is now believed that HIV is the etiological agent of AIDS.

Since the discovery of HIV as the putative etiological agent of AIDS, numerous proposals have been made for anti-HIV chemotherapeutic agents that may be effective in the treatment of AIDS. Thus, for example, European Patent Specification No. 196158 describes 3'-axido-3'-deoxythymidine (which has the approved name zidovudine) and its pharmaceutically acceptable derivatives and their use in the treatment of human retrovirus infections including AIDS. Zidovudine has been found to be of exceptional therapeutic benefit for the treatment of AIDS and related conditions.

In the treatment of AIDS and related conditions, it is generally necessary to administer the anti-HIV chemotherapeutic agent on a continuous regular basis to ensure the maintenance of sufficiently high antiviral levels of the drug in the patient. A problem in maintaining antivirally effective levels of the drug is that very often frequency dosing is required for example up to 6 times per day, particularly with the use of zidovudine which has a half-life of about 1 hour in plasma. Such frequent dosing is inconvenient and may cause problems in ensuring patient compliance.

It is an object of the present invention to provide controlled release pharmaceutical formulations containing as active ingredient 3'-axido-3'-deoxyethymidine in which the release of the active ingredient can be controlled and regulated to allow less frequency dosing.

Thus, according to a feature of the present invention we provide pharmaceutical formulations adapted for oral administration in which discrete units comprising zidovudine are each provided with a controlled release coating comprising a mixture of (a) a non-ionic polymer of at least one monomer selected from alkyl esters of acrylic and methacrylic acids, and (b) ethyl cellulose; components (a) and (b) being present in the coating in a weight ratio of 1:3 to 3:1.

In the coating described above, component (a) is preferably a homopolymer of one or more $C_{1-4}$ alkyl esters of acrylic and/or methacrylic acid, eg. methyl or ethyl acrylate. A particular example of such polymers is that available under the trade name Eudragit NE30D from Rohm Pharma GmbH (Darmstadt, West Germany). Such polymers when used alone, provide a coating which is substantially insoluble in the pH range found in the gastro-intestinal tract but which is permeable to the fluids in the tract to permit some release of drug.

Component (b) in the above coating is preferably applied to the zidovudine cores in the form of an aqueous dispersion for example using a 30% dispersion commercially available under the trade name Aquacoat from FMC Corporation or a 30% dispersion available under the trade name Surlease from Colorcon Ltd.

In general, the above coating preferably comprises components (a) and (b) in a weight ratio of about 1:1. In addition to components (a) and (b), the coating advantageously contains a pore-forming agent to provide further control of the release of zidovudine, for example water-soluble materials such as sodium chloride, polyethylene glycols, lactose, sucrose or preferably mannitol. Such an agent is preferably present in the coating in an amount of 15 to 50% w/w advantageously about 40% w/w. The coating many comprise for example 1–10% w/w. preferably 3–8% of said discrete units.

The above-mentioned discrete units generally take the form of cores comprising zidovudine optionally in admixture with one or more pharmaceutical carries of excipients. Examples of such carries or excipients are well known in the pharmaceutical art for the formulation of tablets and granules and include for example binders, inert diluents, surface active or dispensing agents. Such cores may be prepared for example by admixing zidovudine and any appropriate pharmaceutical carriers or excipients, and compressing or moulding the resulting mixture. Alternatively, zidovudine can be applied to an inert core e.g. a non-pareil or prill, optionally in admixture with one or more appropriate excipients for example in a solution of a binder such a polyvinyl pyrrolidone, followed by drying.

A further alternative form for the core is the formulation of zidovudine with one or more appropriate excipients to produce so-called spheroids i.e. spherical particles having a diameter of 0.5 to 2 mm. Such spherical particles of zidovudine are particularly preferred as the above-mentioned discrete units which are provided with the above-described controlled release coating. In the production of such spheroids, zidovudine and any necessary excipients are mixed with a liquid to form a wet extrudable mass. The mass is then extruded and the extrudate transferred to a spheroniser containing a plate which is rotated generally at 150–2000 rpm depending on the diameter of the plate. The surface of the plate is usually roughened with a regular pattern or grid.

The extrudate is initially broken down by the rotary motion of the plate into short sections or pellets. The material is sufficiently plastic for these pellets to be spheronised by the frictional forces on the plate which gives a rolling motion and also by the interparticulate friction of the revolving pellets. The resulting spheres are removed from the plate and dried before coating.

It will be appreciated that the constitution of the extrudate is critical for the formulations of a material that can be processed to form spheroids of appropriate size and shape. An extrudate having a satisfactory constitution will normally show adequate cohesion and will break up into the required lengths having an essentially smooth surface. If the constitution is incorrect, the extrudate may be too friable or too plastic and will not fragment into short sections having the required length, and thus will not form pellets of essentially uniform diameter.

A constraint on the maximum concentration of drug that can be incorporated in such extrudates, and consequently in the resulting spheroids, is generally the need for a certain minimum amount of excipient(s) in order to ensure workability of the extrudate in the formation of the spheroids. It has been reported that spheroids containing up to 80% w/w/ of theophylline or quinidine sulphate respectively and a specific extrusion aid, namely Avicel RC581, can be obtained. However, such high levels of active ingredients have not generally been reported to be obtainable using other drugs and/or other known extrusion aids. In general extrudates have usually required at least 30% (dry weight) of excipients providing a final maximum concentration of 70% of the drug in the spheroids and previous attempts to prepare spheroids containing high concentrations of drugs of various types have been largely unsuccessful.

We have now found that zidovudine can be successfully combined with extrusion excipients to provide extrudates containing up to 90% or more of drug that still retain workability on spheronisation. Spheroids having desirable handling characteristics and size distribution and containing high concentrations of zidovudine can thereby be obtained.

According to further feature of the present invention we provide pharmaceutical formulations adapted for oral administration in the form of spherical particles having a diameter of 0.5 to 2 mm and comprising a homogeneous mixture of 75–99% w/w of zidovudine as the active ingredient, together with one or more excipients, such particles being especially suitable for coating with a controlled release coating as described above.

The above-mentioned excipient(s) will generally include an extrusion aid, i.e. a material which, when mixed with the desired quantity of zidovudine and an appropriate amount of water or other liquid or solution, provides mixtures that can be extruded and spheronised in conventional manner as described above. Such a material will generally be present in an amount of 1–25% w/w of the spheroid particles.

Particularly preferred examples of such extrusion aids include microcrystalline cellulose described in the U.S. National Formulary, e.g. as sold under the trade namer Avicel, especially microcrystalline cellulose having an average particle size of 50–100µ e.g. Avicel PH101. Such microcrystalline cellulose materials have been found to be particularly advantageous as excipients in the formulations according to the invention in enabling one to prepare by extrusion spherical particles containing high concentrations of drug as referred to above. Other examples of appropriate extrusion aids include those described in Microcrystalline Polymer Science by O.A. Battista, McGraw-Hill (1975) such as microcrystalline collagens and amyuloses, pregelled starch, and also pharmaceutically acceptable clays such as kaolin, bentonite, or attapulgite.

In the spherical particles referred to above, the active ingredient may be present for example in concentrations of at lest 80% w/w and generally less than 95% w/w.

Particularly when the active ingredient is employed in relatively high concentrations, e.g. at least 80% w/w in the spherical particles, it is generally preferred to use a binder to effect satisfactory extrusion and formulation of the spherical particles. Examples of such binders include low viscosity, high-molecular weight water-soluble polymeric material and as polyvinylpyrrolidone, e.g. povidone as described in U.S. National Formulary especially material available commercially as Kollidon K30 and K90, vinylpyrrolidone/vinyl acetate copolymers especially Kollidon VA 64, hydroxypropylmethyl cellulose or sodium carboxymethylcelluose or other cellulose binders. Such binders may generally be present in the spherical particles in amounts of up to 20% w/w, e.g. 2–5% w/w.

Other excipients which may be present in the spherical particles, include for example bulking agents such as lactose, mannitol or sucrose, e.g. in amounts up to 10% w/w.

The spherical particles in the formulations according to the invention advantageously have a diameter of 0.80 to 1.40 mm and are preferably provided with a controlled release coating comprising a non-ionic polymer and ethyl cellulose as described. However, other controlled release coatings may alternatively be employed e.g. mixtures of the acrylic or methacrylic acid or ester polymers referred to above. Such coating materials may be applied to the spherical particles for example in an organic solvent.

According to a further aspect of the present invention, we provide a process for the preparation of the above-described pharmaceutical formulations containing spherical particles which comprises forming an extrudable mass comprising 75 to 99% w/w (dry weight) of zidovudine together with one or more excipients, and a pharmaceutically acceptable liquid, e.g. water, extruding the said mass; subjecting the extrudate to spheronisation to form spherical particles having a diameter of 0.5 to 2 mm; and optionally providing the said spherical particles with a protective coating for example a controlled release coating of the type described above.

In the process according to the invention, the initial step of forming an extrudable mass generally comprises the admixture of the dry ingredients and the pharmaceutically acceptable liquid. If a binder solution is employed, the separate addition of the liquid may not be necessary. In general, the extrudable mass will contain 10 to 40% preferably 20 to 35% (based on the total weight of the mass) of water.

After mixing the ingredients to form an extrudable mass, the mass is then passed through an extruder at an appropriate rate, the extrudate emerging from the aperture(s) of the extruder as long spaghetti-like strands, which break up under their own weight into shorted strands and are further reduced in length and subsequently formed into spherical particles having the desired size in a spheronising apparatus. The spherical particles are then removed from the spheronising apparatus, dried and optionally coated.

The optionally coated discrete units of the pharmaceutical formulations according to the invention are preferably presented in the form of unit doses for example in tablets or capsules, e.g. gelatin capsules, providing a pre-determined specific amount of active ingredient (zidovudine) advantageously 50 to 1000 mg, preferably 100 to 500 mg thereof.

In addition to polymer components (a) and (b) described above, the controlled release coating of the formulations according to the invention may include other appropriate excipients, eg an anti-agglomerating agent such as magnesium stearate, talc, kaolin or colloidal silica, eg Aerosil to prevent sticking of the coated cores.

The coatings may be applied to the discrete units in conventional manner, eg. by suspending the polymer and any other coating components in an appropriate liquid medium such as water, for example forming a dispersion of the polymers which is then applied to the discrete units by spray coating, for example in a fluid bed to form a coating appropriate thickness. Other methods of applying the coatings include pan coating etc.

Zidovudine may be prepared for example as described in the above-mentioned European Patent Specification or by methods known in the art or analogous thereto.

The formulations according to the invention may be employed for the treatment or prophylaxis of various viral infections particularly human retroviral infections such as HIV infections and related conditions such as AID, AIDS-related complex (ARC) and progressive generalised lymphadeopathy (PGL), and AIDS-related neurological conditions such as multiple schlerosis, and tropical spastic paraparesis. Other human retroviral infections include Human T-cell Lymphotropic virus (HTLV)—I and IV and HIV-2 infections.

The invention accordingly provides pharmaceutical formulations according to the invention for use in the treatment or prophylaxis of the above-mentioned human retroviral infections.

The pharmaceutical formulations are generally administered in a dose in the range of 1.0 to 120 mg per kilogram body weight of the recipient per day, preferably in the range of 1.0 to 100 mg per kilogram body weight per day and most preferably in the range 5 to 40 mg per kilogram body weight per day. The desired dose is preferably presented as two, three, or more sub-doses administered at appropriate intervals throughout the day. These sub-doses may be administered in unit dosage form, for example, containing 10 to 1000 mg, and most preferably 100 to 500 mg of active ingredient per unit dosage form. The formulations should be desirably administered to achieve peak plasma concentrations of the active compound of from about 1 to about 100 $\mu$M, preferably about 2 to 50 $\mu$M, most preferably about 3 to about 30 $\mu$M.

The following Examples illustrate the present invention.

EXAMPLE 1

Preparation of Spheroid Cores

Cores were prepared having the following composition:

| | |
|---|---|
| Active Ingredient | 200.0 g |
| Microcrystalline Cellulose (Avicel PH101) | 41.7 g |
| Polyvinylpyrrolidone (Povidone K30) | 8.3 g |
| Purified Water qs | |

EXAMPLE 2

In an analogous manner to that described in Example 1, spheroid cores having the following composition were prepared:

| | |
|---|---|
| Active Ingredient | 212.5 g |
| Microcrystalline Cellulose (Avicel PH101) | 25.0 g |
| Polyvinylpyrrolidone (Povidone K30) | 12.5 g |
| Purified Water q.s | |

EXAMPLE 3

Coating of Spheroid Cores

Coating Composition

| | |
|---|---|
| Eudragit NE30D (30% aqueous dispersion) | 20 g |
| Aquacoat ECD-30 (30% aqueous dispersion) | 20 g |
| Mannitol | 3 g |
| Water | 57 g |

The mannitol was dissolved in the water. The Edragit and Aquacoat were then added with gentle mixing. The coating mixture was applied to 100 g of dry cores prepared as described in Example 1 or 2 using a fluidised bed unit equipped for spray coating. A quantity was applied so as to give a 6% coat. The coated cores were dried and filled into capsules. Dissolution tests were carried out on the cores in the USP rotating paddle apparatus at 50 rpm with water as the dissolution medium. Samples were analysed by UV spectroscopy and % released versus time values calculated:

| Time | % released |
|---|---|
| 30 | 9 |
| 60 | 17 |
| 120 | 33 |
| 180 | 45 |
| 270 | 60 |
| 360 | 71 |

EXAMPLE 4

Capsule Formulation

| Marumes (Spheroid Cores) | mg/capsule |
|---|---|
| Active Ingredient | 300.0 |
| Microcrystalline Cellulose | 61.875 |
| Polyvinylpyrrolidone (Povidone) | 13.125 |
| Purified Water | q.s |
| | 375.0 mg |

| Sustained Release Coating | mg/capsule |
|---|---|
| Eudragit NE30D | 5.625 (Solids) |
| Aquacoat ECD-30 | 5.625 (Solids) |
| Mannitol | 3.750 |
| Purified Talc | q.s |
| Purified Water | q.s |
| Instant Release Marumes | 375.0 |
| Total Fill Weight | 390.0 mg/capsule |

The active ingredient and microcrystalline cellulose are mixed. The povidone is dissolved in purified water and added to the blend to granulate. Marumes are formed by passing the granules through an extruder and a spheronizer. The marumes are dried. The mannitol is dissolved in purified water. The Edragit NE30D and Aquacoat ECD-30 are added and mixed into the solution. The marumes are coated with the suspension, purified talc added to the coated pellets if necessary. The coated pellets are filled in hard-gelatin capsules.

| Capsule Release Profile | |
|---|---|
| Time (min) | % Dissolved |
| 60 | 15.5 |
| 120 | 29.2 |

-continued

Capsule Release Profile

| Time (min) | % Dissolved |
|---|---|
| 180 | 41.8 |
| 240 | 53.8 |
| 360 | 72.2 |
| 480 | 85.0 |
| 720 | 97.2 |

Average of 6 capsules dissolved in 900 ml distilled water by the USP Paddle Method at 50 RPM.

EXAMPLE 5

Capsule Formulation

Marumes (Spheroid Cores)

| | mg/capsule |
|---|---|
| Active Ingredient | 300.0 |
| Microcrystalline Cellulose | 61.9 |
| Polyvinylpyrrolidone (Povidone) | 13.1 |
| Purified Water | q.s |
| | 375.0 mg |
| Sustained Release Coating | |
| Eudragit NE30D (solids) | 5.0625 |
| Aquacoat ECD-30 (solids) | 5.0625 |
| Mannitol | 6.75 |
| Purified Talc | q.s |
| Purified Water | q.s |
| | 16.9 |
| Total Fill Weight | 391.9 mg/capsule |

The capsule formulation was prepared as described in Example 4.

Capsule Release Profile

| Time (min) | % Dissolved |
|---|---|
| 60 | 41 |
| 120 | 73 |
| 180 | 91 |
| 240 | 98 |
| 360 | 101 |

The above release profile was determined as described in Example 4.

EXAMPLE 6

In a similar manner to that described in Example 4, 500 g of marumes (as described in Example 4) are coated with a 6% w/w sustained release coating having one of the following compositions (a), (b) or (c) and the resulting coated marumes are dried at 50° C. for 1 hour.

| Sustained Release Coatings: | | |
|---|---|---|
| (a) | Eudragit RL 100 | 9.55 g |
| | Eudragit RS 100 | 17.75 g |
| | Diethyl phthalate | 2.7 g |
| | Isopropyl alcohol | 90.0 g |
| | Acetone | 60.0 g |
| | Instant release marume | 500.0 g |
| (b) | Ethyl cellulose | 40.0 g |
| | Dibutyl phthalate | 8.0 g |
| | Dichloromethane | 300.0 g |
| | Methanol | 180.0 g |
| | Instant release marume | 500.0 g |
| (c) | Eudragit RS 30D | 75.0 g |
| | Triethyl citrate | 3.0 g |
| | Mannitol | 4.5 g |
| | Purified Water | 80.0 g |
| | Instant release marume | 500.0 g |

We claim:

1. Pharmaceutical formulations adapted for oral administration in which discrete units comprising zidouvdine are each provided with a controlled release coating comprising a mixture of (a) a non-ionic polymer of at least one monomer selected from alkyl esters of acrylic and methacrylic acids, and (b) ethyl cellulose; components (a) and (b) being present in the coating in a weight ratio of 1:3 to 3:1.

2. Pharmaceutical formulations as claimed in claim 1 in which component (a) of the controlled release coating comprises a homopolymer of one or more $C_{1-4}$ alkyl esters of acrylic and/or methacrylic acid.

3. Pharmaceutical formulations as claimed in claim 1 in which the said controlled release coating includes a pore-forming agent.

4. Pharmaceutical formulations as claimed in claim 3 in which the pore-forming agent comprises mannitol.

5. Pharmaceutical formulations as claimed in claim 1 in which components (a) and (b) are present in the coating in a weight ratio of about 1:1.

6. Pharmaceutical formulations as claimed in claim 1 in which the said descrete units comprise spheroids having a diameter of 0.5 to 2 mm.

7. Pharmaceutical formulations adapted for oral administration in the form of spheroids particles having a diameter of 0.5 to 2 mm and comprising a homogeneous mixture of 75–99% of zidovudine as the active ingredient, together with one or more excipients.

8. Pharmaceutical formulations as claimed in claim 7 in which the said spheroids contain at least 80% w/w of Zidouvudine.

9. Pharmaceutical formulations as claimed in claim 7 in which the pharmaceutical excipient includes microcrystalline cellulose.

10. Pharmaceutical formulations as claimed in claim 7 provided with a controlled release coating comprising a mixture of (a) a non-ionic polymer of at least one monomer selected from alkyl esters of acrylic and methacrylic acids, and (b) ethyl celulose; components (a) and (b) being present in the coating in a weight ratio of 1:3 to 3:1.

* * * * *